United States Patent [19]
Takahashi et al.

[11] Patent Number: 5,948,966
[45] Date of Patent: Sep. 7, 1999

[54] GAS SENSOR, METHOD OF MEASURING GAS COMPONENT BY UTILIZING GAS SENSOR, AND METHOD OF DIAGNOSING MALFUNCTION OF EXHAUST GAS PURIFYING APPARATUS

[75] Inventors: Tomonori Takahashi, Chita; Naoyuki Ogawa, Nagoya, both of Japan

[73] Assignee: NGK Insulators, Ltd., Japan

[21] Appl. No.: 08/986,798

[22] Filed: Dec. 8, 1997

[30] Foreign Application Priority Data

Dec. 10, 1996 [JP] Japan ................................. 8-329619

[51] Int. Cl.⁶ .................................................. G01N 27/00
[52] U.S. Cl. ...................... 73/23.31; 73/31.05; 204/424; 204/427; 422/94
[58] Field of Search ............... 73/23.31, 23.32, 73/31.05; 204/424, 426, 427, 428; 422/90, 94, 98

[56] References Cited

U.S. PATENT DOCUMENTS 5,143,696  9/1992  Haas et al. ..................... 324/663 X

FOREIGN PATENT DOCUMENTS

| 61-11653 | 1/1986 | Japan | 73/23.32 |
| 3-216546 | 9/1991 | Japan | 73/23.32 |
| 5-2645501 | 10/1993 | Japan | 73/23.32 |

*Primary Examiner*—Daniel S. Larkin
*Attorney, Agent, or Firm*—Wall Marjama Bilinski & Burr

[57] ABSTRACT

A gas sensor for measuring a specific gas component, especially hydrocarbons, in a gas to be measured, including a hydrocarbon prevention filter preferably made of zeolite. An oxygen concentration difference between (1) an oxygen concentration in a gas to be measured from which hydrocarbons are removed by the hydrocarbon prevention filter and further combustible components are removed and (2) a known oxygen concentration or an oxygen concentration in a gas from which only combustible components are removed, is calculated. Once an oxygen amount necessary for a combustion of hydrocarbons is calculated, it is possible to measure a hydrocarbon concentration in a gas to be measured on the basis of the thus calculated oxygen amount.

11 Claims, 7 Drawing Sheets

FIG_3

FIG_5
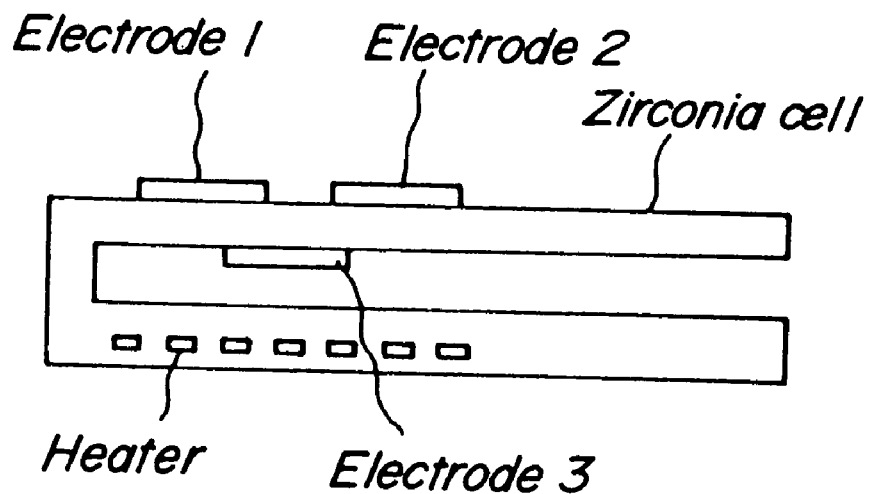
FIG_6
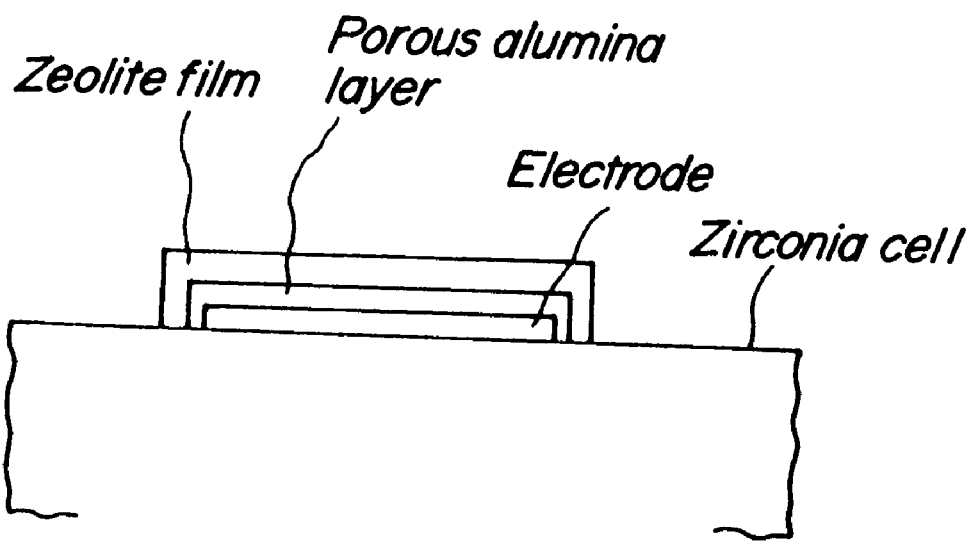

FIG_8
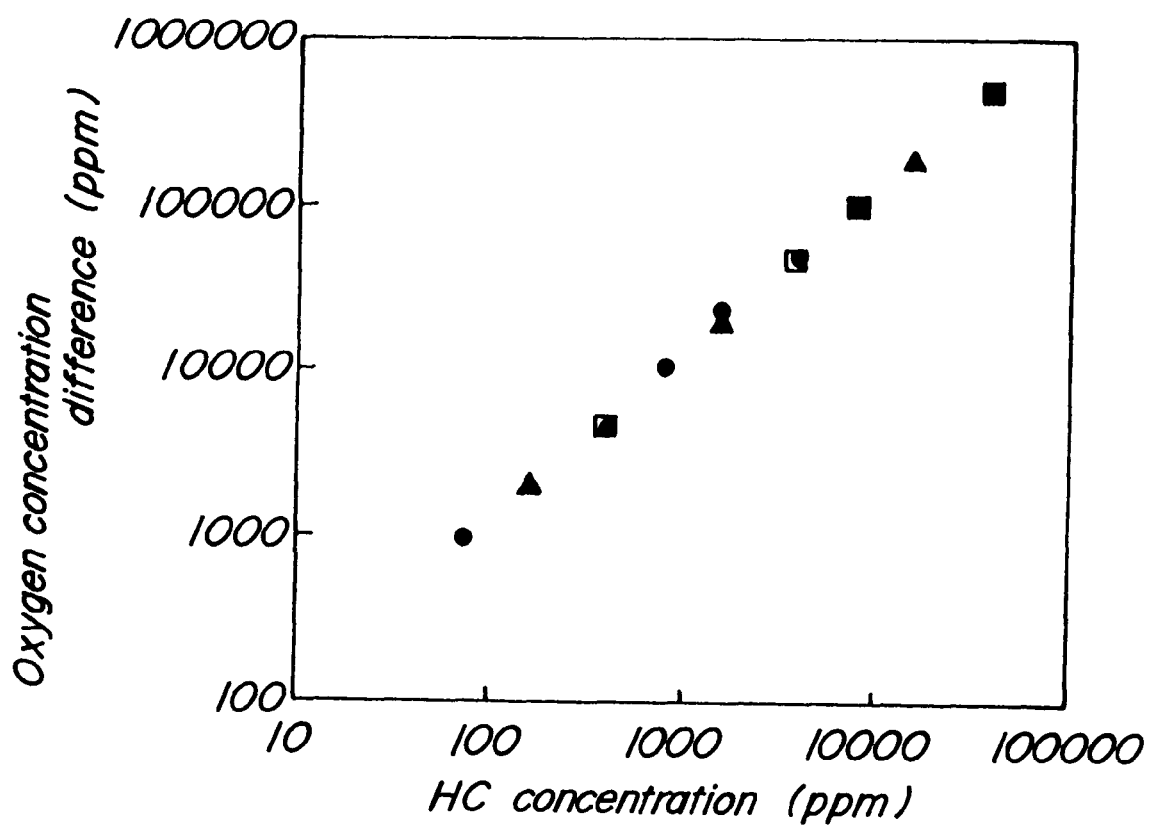

GAS SENSOR, METHOD OF MEASURING GAS COMPONENT BY UTILIZING GAS SENSOR, AND METHOD OF DIAGNOSING MALFUNCTION OF EXHAUST GAS PURIFYING APPARATUS

BACKGROUND OF THE INVENTION

1. Field of the Invention

The present invention relates to a gas sensor used for measuring a concentration of a specific gas component, especially hydrocarbons, in an exhaust gas generated from, for example, automobiles, a method of measuring a gas component by utilizing such a gas sensor, and a method of diagnosing a malfunction of an exhaust gas purifying apparatus.

2. Related Art Statement

Recently, there is a requirement that a malfunction of an exhaust gas purifying apparatus provided at a downstream position of an automobile engine be detected and reported to the driver of the automobile. This kind of malfunction can be detected by measuring an increase of hydrocarbon concentration in an exhaust gas passing through the exhaust gas purifying apparatus. In order to limit such an increase of hydrocarbon concentration, there is OBDII in California, in which a total amount of NMHC (non methane hydrocarbon) is limited under a predetermined level. Therefore, there is a necessity for measuring a concentration of hydrocarbon in the exhaust gas of automobiles.

Usually, as a gas sensor for measuring a concentration of hydrocarbon in a gas to be measured, a total hydrocarbon analyzer utilizing a hydrogen flame ionization method is known. This total hydrocarbon analyzer measures a hydrocarbon concentration by supplying hydrocarbons into a hydrogen flame to perform an ionization, measuring such an ionization as a small ion current by applying DC voltage between electrodes which sandwich the hydrogen flame, and calculating the hydrogen concentration from the thus measured small ion current.

In the total hydrocarbon analyzer for measuring an HC (hydrocarbon) concentration mentioned above, it is possible to measure accurately the HC concentration in the exhaust gas. However, in the total hydrocarbon analyzer utilizing a hydrogen flame ionization method, it is necessary to use hydrogen, and also it is necessary to use a large and complicated mechanism. As a result, it is not possible to construct a compact sensor which can be used in automobiles by the total hydrocarbon analyzer.

SUMMARY OF THE INVENTION

An object of the invention is to eliminate the drawbacks mentioned above and to provide a gas sensor which can perform an accurate concentration measurement even if the sensor size is compact, a method of measuring a gas component by utilizing such a gas sensor, and a method of diagnosing a malfunction of an exhaust gas purifying apparatus by utilizing such a gas sensor.

According to a first aspect of a gas sensor of the invention, the gas sensor for measuring a hydrocarbon concentration in a gas to be measured, comprises: a sensor portion which includes a hydrocarbon prevention filter for preventing passage of hydrocarbons; a combustion catalyst for removing combustible components in a gas to be measured which is passed through said hydrocarbon prevention filter; and an oxygen measurement means for measuring an oxygen concentration of a gas to be measured from which said combustible components are removed by said combustion catalyst.

According to a first aspect of a method of measuring a gas component of the invention, the method of measuring a hydrocarbon concentration in a gas to be measured by utilizing the first aspect of the gas sensor according to the invention, comprises the steps of: measuring an oxygen concentration in a gas to be measured, from which hydrocarbons are removed by said hydrocarbon prevention filter and further combustible components are removed by said combustion catalyst, by said oxygen measurement means; calculating an oxygen concentration difference between said oxygen concentration measured in a gas to be measured, from which only combustible components are removed; and calculating a hydrocarbon concentration in a gas to be measured on the basis of the thus obtained oxygen concentration difference.

According to a second aspect of the gas sensor of the invention, the gas sensor for measuring a hydrocarbon concentration in a gas to be measured, comprises: a first sensor portion including a hydrocarbon prevention filter for preventing passage of hydrocarbons, a first combustion catalyst for removing combustible components in a gas to be measured which is passed through said hydrocarbon prevention filter, and a first oxygen measurement means for measuring a first oxygen concentration in a gas to be measured from which said combustible components are removed by said first combustion catalyst; a second sensor portion including a second combustion catalyst for removing combustible components in a gas to be measured, and a second oxygen measurement means for measuring a second oxygen concentration in a gas to be measured from which said combustible components are removed by said second combustion catalyst; and a process means for calculating an oxygen concentration difference between said first oxygen concentration measured by said first oxygen measurement means and said second oxygen concentration measured by said second oxygen measurement means and then calculating a hydrocarbon concentration in a gas to be measured on the basis of the thus calculated oxygen concentration difference.

According to a second aspect of a method of measuring a gas component of the invention, the method of measuring a hydrocarbon concentration in a gas to be measured by utilizing the first aspect of the gas sensor according to the invention, comprises the steps of: measuring a first oxygen concentration in a gas to be measured, from which hydrocarbons are removed by said hydrocarbon prevention filter and further combustible components are removed by said first combustion catalyst, by said first oxygen measurement means; measuring a second oxygen concentration in a gas to be measured, from which combustible components are removed by said second combustion catalyst, by said second oxygen measurement means; calculating an oxygen concentration difference between said first oxygen concentration measured by said first oxygen measurement means and said second oxygen concentration measured by said second oxygen measurement means; and calculating a hydrocarbon concentration in a gas to be measured on the basis of the thus calculated oxygen concentration difference.

According to a third aspect of a gas sensor for diagnosing a malfunction of an exhaust gas purifying apparatus in automobiles, the sensor comprises: a hydrocarbon prevention filter for preventing passage of hydrocarbons, a combustion catalyst for removing combustible components in a gas to be measured which is passed through said hydrocarbon prevention filter, and an oxygen measurement means for measuring an oxygen concentration of a gas to be measured from which said combustible components are removed by said combustion catalyst; and an indication means for indicating a malfunction of said exhaust gas purifying apparatus for a driver, when an oxygen concentration difference between said oxygen concentration in a gas measured by said oxygen measurement means and an oxygen concentration in a gas measured by an oxygen sensor for controlling an air/fuel ratio in an engine reaches to an oxygen concentration equivalent to a regulation level of hydrocarbons.

According to the invention, a method of diagnosing a malfunction of an exhaust gas purifying apparatus by utilizing the third aspect of the gas sensor according to the invention, comprises the steps of: using said oxygen measurement means to measure an oxygen concentration in an exhaust gas passed through said exhaust gas purifying apparatus, from which hydrocarbons are removed by said hydrocarbon prevention filter and further combustible components are removed by said combustion catalyst, calculating an oxygen concentration difference between said oxygen concentration measured by said oxygen measurement means and an oxygen concentration measured by said oxygen sensor for controlling an air/fuel ratio of an engine; and indicating a malfunction of said exhaust gas purifying apparatus for a driver when the thus calculated oxygen concentration difference reaches to an oxygen concentration equivalent to a regulation level of hydrocarbons.

In the present invention, the hydrocarbon prevention filter preferably made of zeolite is used. Therefore, if an oxygen concentration difference between an oxygen concentration in a gas to be measured from which hydrocarbons are removed by the hydrocarbon prevention filter and further combustible components are removed and a known oxygen concentration (first aspect of the invention) or an oxygen concentration in a gas from which only combustible components are removed (second aspect of the invention), and an oxygen amount necessary for a combustion of hydrocarbons is calculated, it is possible to measure a hydrocarbon concentration in a gas to be measured on the basis of the thus calculated oxygen amount.

Moreover, in the present invention, if an oxygen concentration difference between an oxygen concentration in an exhaust gas at a downstream of an exhaust gas purifying apparatus from which hydrocarbons are removed by the hydrocarbon prevention filter and further combustible components are removed and an oxygen concentration in an exhaust gas which is not passed through the exhaust gas purifying apparatus, and an oxygen amount necessary for a combustion of hydrocarbons is calculated, it is possible to inform a driver of a malfunction of the exhaust gas purifying apparatus, preferably by an ON light when the thus calculated oxygen amount reaches an oxygen amount equivalent to a regulation level of hydrocarbons.

BRIEF DESCRIPTION OF THE DRAWING

FIG. 5 is a schematic view showing one step of a gas sensor manufacturing method in the present invention;

FIG. 6 is a schematic view illustrating an electrode construction of the gas sensor according to the present invention;

FIG. 8 is a graph showing a relation between oxygen concentration difference and HC concentration.

DESCRIPTION OF THE PREFERRED EMBODIMENTS

Figure 1:
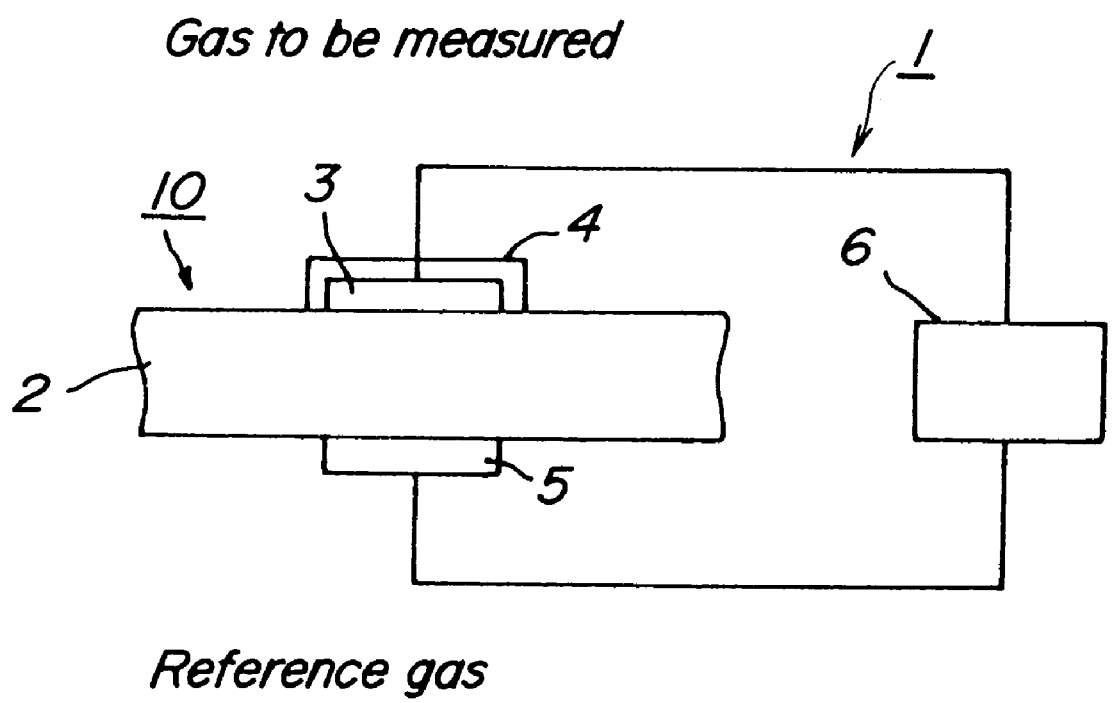
FIG. 1 is a schematic view showing one embodiment of a gas sensor according to the present invention.

FIG. 1 is a schematic view showing one embodiment of a gas sensor according to a first aspect of the invention. In the embodiment shown in FIG. 1, a gas sensor 1 comprises a sensor portion 10 and a process portion 6. The sensor portion 10 comprises an oxygen ion conduction member 2; a measurement electrode 3 arranged on one main plane of the oxygen ion conduction member 2, which is disposed to a gas to be measured; a hydrocarbon prevention filter 4 arranged on the measurement electrode 3 for preventing passage of hydrocarbons; and a reference electrode 5 arranged on the other main plane of the oxygen ion conduction member 2, which is exposed to a reference gas. In this embodiment, the measurement electrode 3 is made of platinum and serves as a combustion catalyst. In the process portion 6, an oxygen concentration in a gas, from which hydrocarbons are removed by the hydrocarbon prevention filter 4 and further combustible components are removed by the measurement electrode 3, is measured on the basis of an electromotive force generated between the measurement electrode 3 and the reference electrode 5. An oxygen concentration difference between the thus measured oxygen concentration and an oxygen concentration measured preliminarily in a gas from which only combustible components are removed, is then destroyed so that a hydrocarbon concentration in a gas to be measured can be obtained on the basis of the thus calculated oxygen concentration difference.

In the embodiment shown in FIG. 1, the gas sensor 1 is constructed by the sensor portion 10 and the process portion 6. However, in the case that the oxygen concentration measured preliminarily in a gas from which combustible components including hydrocarbon are removed is a standard value such as 0, the oxygen concentration measured by the sensor portion 10 shows directly the oxygen concentration difference mentioned above. In this case, the gas sensor 1 according to a first aspect of the invention may be constructed by the sensor portion 10 only.

As the hydrocarbon prevention filter 4, it is preferred to use a zeolite membrane. The zeolite membrane is generally known in this technical field, and a filtering property of the zeolite membrane can be selected by using a hydrothermal synthesis method. Therefore, in this embodiment, the hydrocarbon prevention filter 4 is designed to have a filtering property such that various kinds of hydrocarbon molecules in a gas to be measured are not passed, but other molecules except for the hydrocarbon molecules are passed. Moreover, as the oxygen ion conduction member 2, it is preferred to use zirconia. Further, as the measurement electrode 3 and the reference electrode 5, it is preferred to use a platinum electrode. In this embodiment, the gas sensor 1 having the construction shown in FIG. 1 is used in an atmosphere in which the oxygen concentration after a combustion of the combustible components is previously known. Therefore, it is possible to detect the hydrocarbon concentration from the oxygen concentration difference between the oxygen concentration measured by the sensor portion 10 and the oxygen concentration after the combustion of the combustible components.

Figure 2:
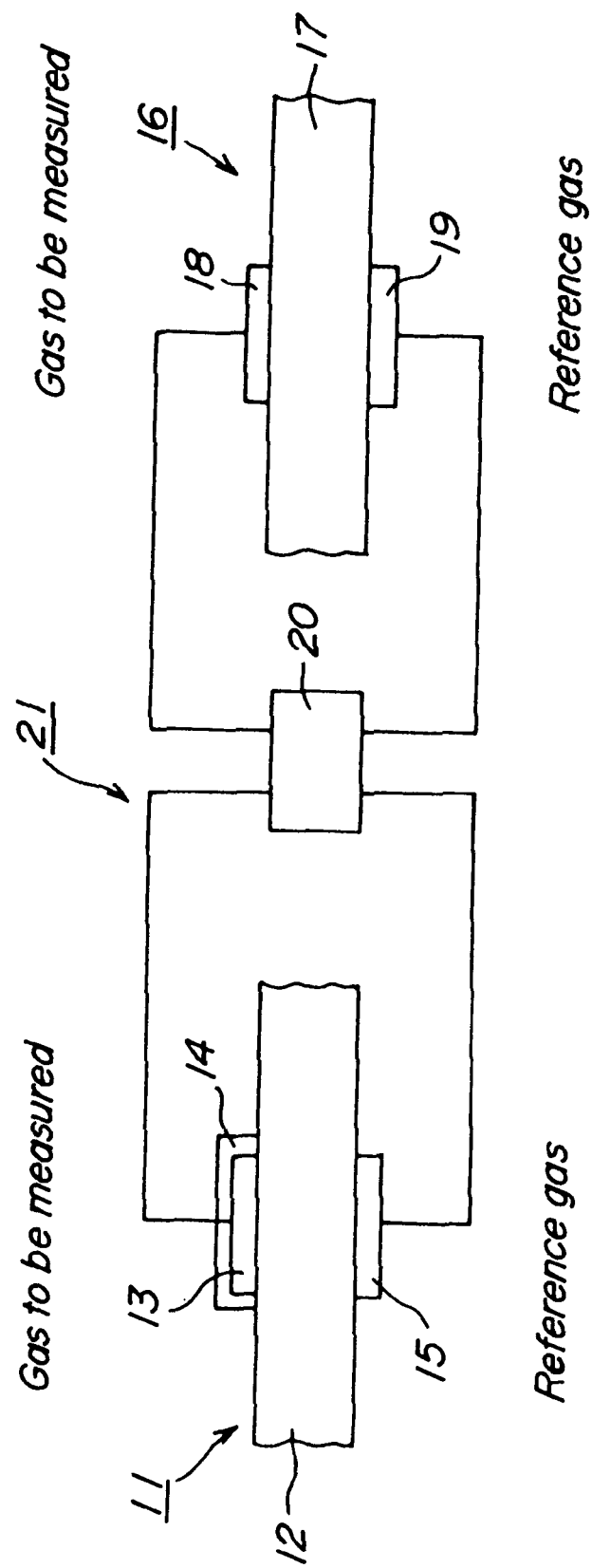
FIG. 2 is a schematic view illustrating another embodiment of the gas sensor according to the present invention.

FIG. 2 is a schematic view showing one embodiment of a gas sensor according to the second aspect of the invention.

In the embodiment shown in FIG. 2, a gas sensor 21 comprises a first gas sensor 11, a second gas sensor 16, and a process portion 20. The first gas sensor 11 comprises an oxygen ion conduction member 12; a measurement electrode 13 arranged on one main plane of the oxygen ion conduction member 12, which is exposed to a gas to be measured; a hydrocarbon prevention filter 14 arranged on the measurement electrode 13 for preventing a pass of hydrocarbons; and a reference electrode 15 arranged on the other main plane of the oxygen ion conduction member 12, which is exposed to a reference gas. Moreover, the second gas sensor 16 having the same construction as the known one comprises an oxygen ion conduction member 17; a measurement electrode 18 arranged on one main plane of the oxygen ion conduction member 17, which is exposed to a gas to be measured; and a reference electrode 19 arranged on the other main plane of the oxygen ion conduction member 17, which is exposed to a reference gas. Further, in the process portion 20, an oxygen concentration difference between the oxygen concentration in a gas measured by the first gas sensor 11 and the oxygen concentration in a gas measured by the second gas sensor 16 is calculated, and a hydrocarbon concentration in a gas to be measured is calculated on the basis of the thus calculated oxygen concentration difference. In the embodiment shown in FIG. 2, the measurement electrode 13 serves as a first combustion catalyst, and the measurement electrode 18 serves as a second combustion catalyst.

As the hydrocarbon prevention filter 14, as is the same as the embodiment shown in FIG. 1, it is preferred to use a zeolite membrane. The zeolite membrane is generally known in this technical field, and a filtering property of the zeolite membrane can be selected by using a hydrothermal synthesis method. Therefore, in this embodiment, the hydrocarbon prevention filter 14 is designed to have a filtering property such that various kinds of hydrocarbon molecules in a gas to be measured are not passed but the other molecules except for the hydrocarbon molecules are passed. Moreover, as the oxygen ion conduction members 12 and 17, it is preferred to use zirconia. Further, as the measurement electrodes 13 and 18 and the reference electrodes 15 and 19, it is preferred to use a platinum electrode.

Figure 3:
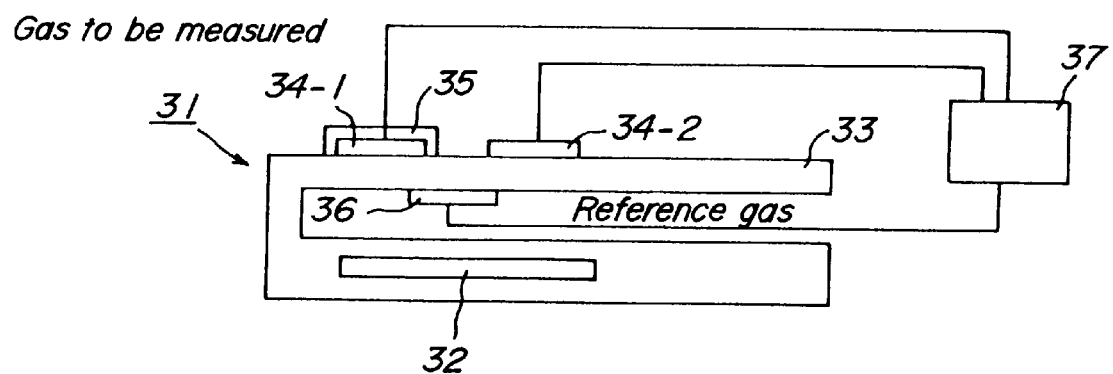
FIG. 3 is a schematic view depicting still another embodiment of the gas sensor according to the present invention.

FIG. 3 is a schematic view showing still another embodiment of a gas sensor according to the invention. In this embodiment, as compared with the embodiment shown in FIG. 2, it is different that the first gas sensor and the second gas sensor are formed on the same oxygen ion conduction member. That is to say, in the embodiment shown in FIG. 3, a gas sensor 31 comprises an oxygen ion conduction member 33 having a heater 32; a first measurement electrode 34-1 and a second measurement electrode 34-2 arranged on one main plane of the oxygen ion conduction member 33; a hydrocarbon prevention filter 35 arranged on the first measurement electrode 34-1; and a reference electrode 36 arranged on the other main plane of the oxygen ion conduction member 33. In this embodiment, materials used for respective portions are not limited. However, it is preferred to use zirconia as the oxygen ion conduction member 33, platinum as the first measurement electrode 34-1 and the second measurement electrode 34-2, and a zeolite membrane as the hydrocarbon prevention filter 35.

In the embodiment mentioned above, the first measurement electrode 34-1 and the reference electrode 36 construct a first sensor portion, and the second measurement electrode 34-2 and the reference electrode 36 construct a second sensor portion. Moreover, numeral 37 shows a process portion in which an oxygen concentration difference between an oxygen concentration in a gas measured by the first sensor portion and an oxygen concentration in a gas measured by the second sensor portion is calculated, and a hydrocarbon concentration is calculated on the basis of the thus calculated oxygen concentration difference. Moreover, in the embodiment shown in FIG. 3, the first measurement electrode 34-1 serves as a first combustion catalyst and the second measurement electrode 34-2 serves as a second combustion catalyst.

Figure 4:
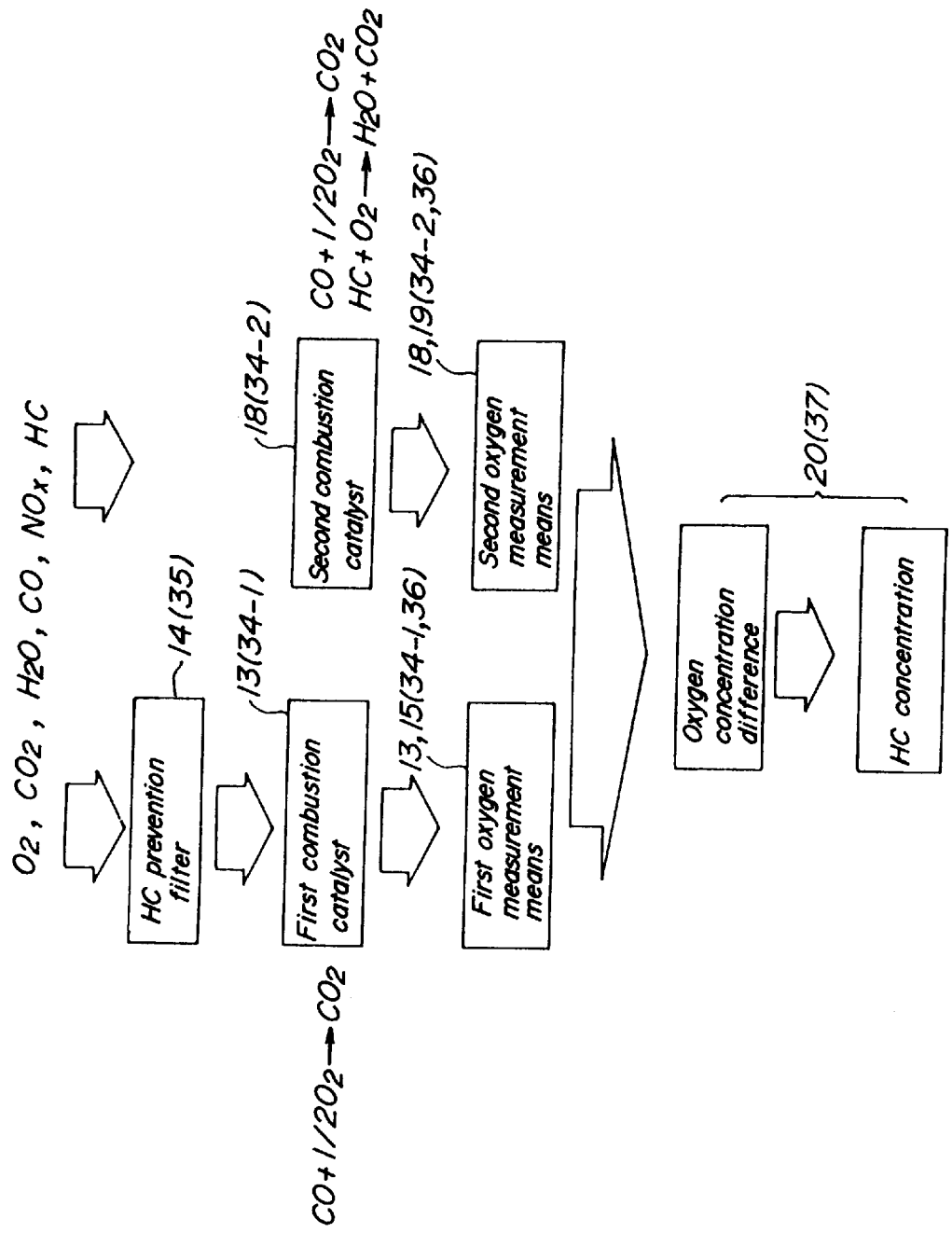
FIG. 4 is a schematic view for explaining a method of measuring a hydrocarbon concentration by utilizing the gas sensor shown in FIGS. 2 and 3.

FIG. 4 is a schematic view for explaining a method of measuring a hydrocarbon concentration by utilizing the gas sensor having the construction shown in FIGS. 2 and 3. At first, a gas to be measured which includes $O_2$, $CO_2$, $H_2O$, CO, NOx, HC, and so on is brought into contact with the first measurement electrode 13(34-1) serving also as the first combustion catalyst and the second measurement electrode 18(34-2) serving also as the second combustion catalyst. In this case, since a gas supplied to the first measurement electrode 13(34-1) is passed through the hydrocarbon prevention filter 14 (35), hydrocarbons are removed from that gas Then, when a gas to be measured is brought into contact with the first measurement electrode 13(34-1) and the second measurement electrode 18(34-2), combustible components in the gas are burnt and removed. In this case, a CO component is burnt at the first combustion catalyst 13(34-1), and CO and hydrocarbon (HC) components are burnt at the second combustion catalyst 18(34-2).

Then, a first oxygen concentration in a gas to be measured, in which combustible components except for HC component are burnt, is measured by a first oxygen measurement means consisting of the first measurement electrode 13(34-1) and the reference electrode 15(36). In addition, a second oxygen concentration in a gas to be measured, in which combustible components including HC component are burnt, is measured by a second oxygen measurement means consisting of the second measurement electrode 18(34-2) and the reference electrode 19(36). Then, in the process portions 20(37), an oxygen concentration difference between the first oxygen concentration and the second oxygen concentration is calculated. The thus calculated oxygen concentration difference shows an oxygen amount necessary for burning hydrocarbons (HC). Therefore, if a relation between the oxygen amount necessary for burning hydrocarbons and a hydrocarbon amount, i.e. a hydrocarbon concentration, is preliminarily measured, it is possible to calculate a hydrocarbon concentration from the oxygen concentration difference on the basis of the thus preliminarily measured relation.

In the embodiments mentioned above, the gas sensor is utilized for measuring a hydrocarbon concentration in a gas to be measured. According to the invention, it is further possible to diagnose a malfunction of an exhaust gas purifying apparatus in automobiles by utilizing a gas sensor having the same construction as that of the embodiments mentioned above. In this case, it is assumed that a malfunction of the exhaust gas purifying apparatus is dependent upon an increase of a hydrocarbon concentration in an exhaust gas which passes through the exhaust gas purifying apparatus. Then, a malfunction of the exhaust gas purifying apparatus is communicated to a driver by means of an indication light (e.g., an ON light) when an oxygen amount equivalent to a regulation level of a hydrocarbon concentration reaches to a predetermined value. That is to say, the gas sensor 1 having a construction shown in FIG. 1 is arranged at a downstream position of the exhaust gas purifying apparatus in automobiles, and an oxygen concentration of the exhaust gas passed through the exhaust gas purifying apparatus is measured by the gas sensor 1. Then, an oxygen concentration difference between the thus measured oxygen concentration and an oxygen concentration in the exhaust gas measured by an oxygen sensor used for controlling an air/fuel ratio in an engine (which sensor is arranged at an upstream position of the exhaust gas purifying apparatus but at a downstream position of the engine) is calculated, and an oxygen amount necessary for a combustion of hydrocarbons is calculated on the basis of the thus calculated oxygen concentration difference. Then, a malfunction of the exhaust gas purifying apparatus is communicated to a driver by, for example, an ON light. The gas sensor according to the third aspect of the invention mentioned above can be applied for OBDII.

Hereinafter, an actual example will be explained.

EXAMPLE (1) Manufacture of the gas sensor:

A gas sensor having a hydrocarbon prevention filter made of a zeolite membrane was manufactured as follows. At first, as shown in FIG. 5, a base oxygen sensor was manufactured according to a known manufacturing method. This type of gas sensor is referred to as a TF HEGO (Thick Film Exhaust Gas Oxygen) sensor. Then, alumina was coated on an electrode 1 by a thermal spraying method to provide a porous alumina layer having a thickness of 100 μm on the electrode 1 only. Then, a strip paint was arranged on the portion except for the electrode 1 on which the porous alumina layer was provided.

After that, the gas sensor was dipped in a sol solution including a zeolite raw material, and was dried for 5 hours at 90° C. As the sol solution including a zeolite raw material, a colloidal silica was used for Si raw material, aluminum sulfate was used for Al raw material, and sodium hydroxide was used for Na raw material. Moreover, the sol solution was prepared by adjusting $SiO_2/Al_2O_3$ to 25 and $Na_2O/Al_2O_3$ to 0.34 to obtain a water amount of 85%. Then, the strip paint was peeled off to obtain a gas sensor in which only the electrode 1 made of porous alumina layer was coated by a zeolite raw material. Then, an autoclave treatment was performed for the gas sensor.

The autoclave treatment was performed by a hydrothermal treatment for 96 hours at 180° C. under the condition such that triethylamine and ethylene diamine were used as a template material. Then, the gas sensor was cooled in the autoclave, and then a boiling wash treatment was performed three times with respect to the gas sensor picked up from the autoclave, using fresh distilled water each time. After the gas sensor was dried, in order to remove the template material provided in micro holes of zeolite, calcination was performed for 5 hours at 500° C. A cross section of the electrode 1 manufactured as mentioned above is shown in FIG. 6. In this case, it was confirmed by means of XRD that the thus manufactured zeolite was ZSM-5.

Figure 7:
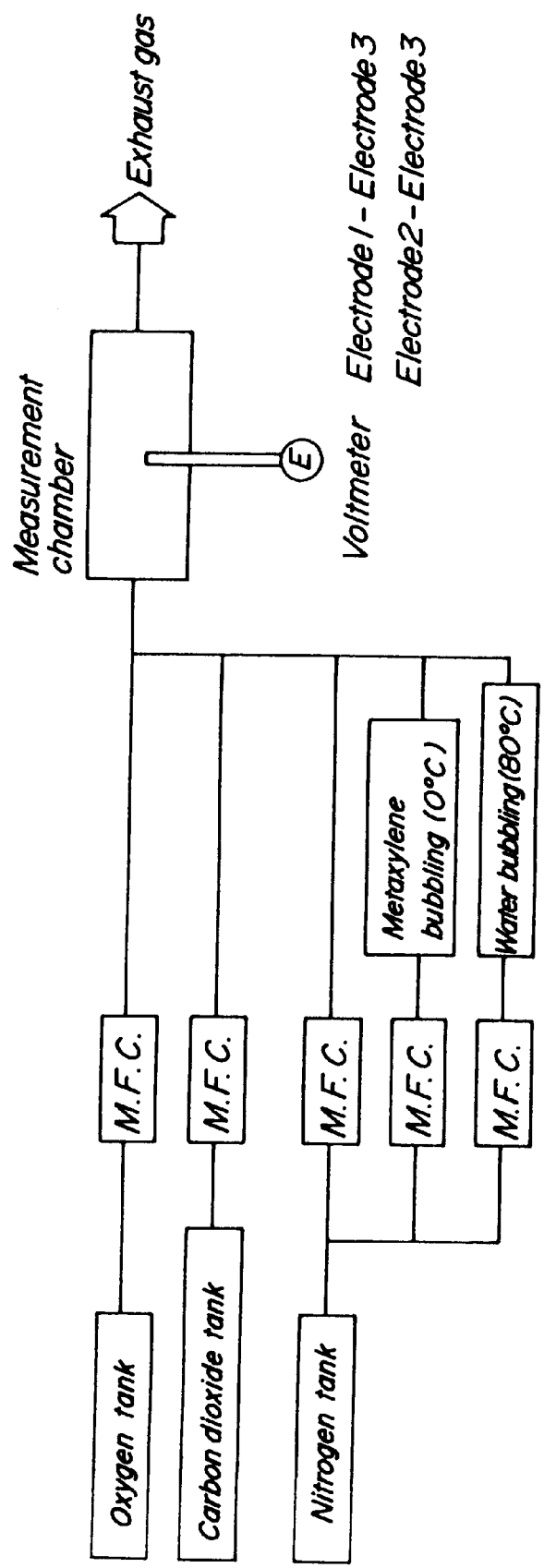
FIG. 7 is a schematic view depicting one embodiment of an apparatus which is used for an examination of a hydrocarbon measurement in the present invention.

(2) Measuring of hydrocarbons by the thus manufactured gas sensor:

An apparatus used for this examination, in which m-xylene was used as a hydrocarbon (HC) to be measured, was shown in FIG. 7. An examination gas was prepared by means of mass-flow controllers to obtain compositions shown in the following Table 1 and Table 2. Then, the thus prepared examination gas was introduced into a measurement chamber in which the gas sensor manufactured according to the above (1) step was arranged. In this case, a bubbling treatment at 0° C. was performed with respect to m-xylene by using a nitrogen gas. By utilizing this bubbling treatment, a nitrogen component was introduced into the measurement chamber as a carrier gas. The gas sensor was preliminarily heated at 800° C. by a heater provided in the measurement chamber. Then, electromotive forces generated between the electrode 1 and the electrode 3 and between the electrode 2 and the electrode 3 were measured respectively by a voltmeter, and the thus measured electromotive force was converted into an oxygen concentration on the basis of the Nernst equation. Moreover, actual hydrocarbon concentration (HC concentration) of the same examination gas was measured by a hydrogen flame type HC analyzer.

TABLE 1

| m-xylene (ppm) | 10 | 50 | 100 | 200 | 500 | 1000 | 5000 |
|---|---|---|---|---|---|---|---|
| oxygen (%) | 5 | 5 | 5 | 5 | 5 | 5 | 5 |
| carbon dioxide (%) | 10 | 10 | 10 | 10 | 10 | 10 | 10 |
| water (%) | 10 | 10 | 10 | 10 | 10 | 10 | 10 |
| nitrogen | remainder | remainder | remainder | remainder | remainder | remainder | remainder |

TABLE 2

| m-xylene (ppm) | 20 | 200 | 2000 | 50 | 500 | 1000 | 5000 |
|---|---|---|---|---|---|---|---|
| oxygen (%) | 10 | 10 | 10 | 5 | 5 | 5 | 5 |
| carbon dioxide (%) | 10 | 10 | 10 | 20 | 20 | 20 | 20 |
| water (%) | 10 | 10 | 10 | 10 | 10 | 10 | 10 |
| nitrogen | remainder | remainder | remainder | remainder | remainder | remainder | remainder |

The measurement results are shown in Table 3 and FIG. 8 respectively. In Table 3 and FIG. 8, a symbol ● shows a relation between an HC concentration measured by the hydrogen flame type HC analyzer and an oxygen concentration difference measured by the gas sensor according to the invention in the case that a m-xylene concentration is varied in an range of 10–5000 ppm in an examination gas including 5% oxygen, 10% carbon dioxide and 10% water. Moreover, a symbol ▲ and a symbol □ show the same relation in the same examination gas except for an oxygen concentration of 10% (▲) and a carbon dioxide concentration of 20% (□). As clearly understood from FIG. 8, all the cases mentioned above have an excellent linearity between the HC concentration and the oxygen concentration difference. Therefore, it is understood that a m-xylene concentration can be measured on the basis of the oxygen concentration difference measured by the gas sensor according to the invention.

TABLE 3

| HC concentration (ppm) | oxygen concentration difference (ppm) | | |
|---|---|---|---|
| | ● | ▲ | □ |
| 75 | 960 | | |
| 407 | 4500 | | |
| 800 | 10500 | | |
| 1580 | 23000 | | |
| 4015 | 50087 | | |
| 8002 | 102119 | | |
| 39880 | 505033 | | |
| 164 | | 2080 | |
| 1589 | | 20500 | |

TABLE 3-continued

| HC concentra- tion (ppm) | oxygen concentration difference (ppm) | | |
|---|---|---|---|
| | ● | ▲ | □ |
| 15788 | | 201330 | |
| 399 | | | 4650 |
| 3897 | | | 48900 |
| 8055 | | | 102500 |
| 40123 | | | 495750 |

In this examination, ZSM-5 membrane was used as the hydrocarbon prevention filter and metaxylene was used as a hydrocarbon to be measured. However, it is possible to measure various kinds of hydrocarbons by suitably selecting a zeolite having a suitable diameter for a hydrocarbon to be measured from A-type zeolite, X-type zeolite, Y-type zeolite, DD3R, DOH, silica soda light, and so on. Moreover, in this examination, only metaxylene was used as a hydrocarbon to be measured. However, in the case that more than two kinds of hydrocarbons are mixed to form a mixed gas, if a relation between an oxygen concentration difference according to the invention in the mixed gas and an amount of oxygen necessary for burning the mixed gas is preliminarily obtained, a hydrocarbon concentration of the mixed gas in which more than two kinds of hydrocarbons are mixed can be measured in the same manner as mentioned above.

As clearly understood from the above explanations, according to the invention, the hydrocarbon prevention filter preferably made of zeolite is used. Therefore, if an oxygen concentration difference between an oxygen concentration in a gas to be measured from which hydrocarbons are removed by the hydrocarbon prevention filter and further combustible components are removed and a known oxygen concentration or an oxygen concentration in a gas from which only combustible components are removed, and an oxygen amount necessary for a combustion of hydrocarbons is calculated, it is possible to measure a hydrocarbon concentration in a gas to be measured on the basis of the thus calculated oxygen amount. Moreover, since the gas sensor for measuring a hydrocarbon concentration in a gas to be measured according to the invention can be constructed on the basis of a small oxygen sensor, it is possible to form the gas sensor according to the invention in a compact manner, and thus the gas sensor according to the invention can be installed in automobiles. Further, the gas sensor according to the invention can be utilized for a diagnosis of a malfunction of the exhaust gas purifying apparatus in automobiles.

What is claimed is:

1. A gas sensor for measuring a hydrocarbon concentration in a gas to be measured, comprising: a sensor portion which includes a hydrocarbon prevention filter for preventing passage of hydrocarbons therethrough; a combustion catalyst for removing combustible components from the gas to be measured which is passed through said hydrocarbon prevention filter; and oxygen measurement means for measuring an oxygen concentration of the gas to be measured from which the combustible components have been removed by said combustion catalyst.

2. The gas sensor according to claim 1, wherein said oxygen measurement means comprises: an oxygen ion conduction member; a measurement electrode arranged on one main plane of said oxygen ion conduction member, which is exposed to the gas to be measured; and a reference electrode arranged on the other main plane of said oxygen ion conduction member, which is exposed to a reference gas; wherein said measurement electrode functions as said combustion catalyst.

3. The gas sensor according to claim 1, wherein said hydrocarbon prevention filter comprises a zeolite membrane.

4. A method of measuring a hydrocarbon concentration in a gas to be measured by utilizing the gas sensor set forth in claim 1, comprising the steps of: using said oxygen measurement means to measure an oxygen concentration in a gas to be measured, from which hydrocarbons are removed by said hydrocarbon prevention filter and further combustible components are removed by said combustion catalyst; calculating an oxygen concentration difference between said oxygen concentration measured and an oxygen concentration in a gas to be measured from which only combustible components are removed; and calculating a hydrocarbon concentration in a gas to be measured on the basis of the thus obtained oxygen concentration difference.

5. A gas sensor for measuring a hydrocarbon concentration in a gas to be measured, comprising: a first sensor portion including a hydrocarbon prevention filter for preventing passage of hydrocarbons therethrough, a first combustion catalyst for removing combustible components from the gas to be measured which is passed through said hydrocarbon prevention filter, and a first oxygen measurement means for measuring a first oxygen concentration in the gas to be measured from which said combustible components are removed by said first combustion catalyst; a second sensor portion including a second combustion catalyst for removing combustible components from the gas to be measured, and a second oxygen measurement means for measuring a second oxygen concentration in the gas to be measured from which said combustible components are removed by said second combustion catalyst; and process means for calculating an oxygen concentration difference between said first oxygen concentration measured by said first oxygen measurement means and said second oxygen concentration measured by said second oxygen measurement means and then calculating a hydrocarbon concentration in the gas to be measured on the basis of the thus calculated oxygen concentration difference.

6. The gas sensor according to claim 5, wherein said first oxygen measurement means and said second oxygen measurement means each comprises: an oxygen ion conduction member; a measurement electrode arranged on one main plane of said oxygen ion conduction member, which is exposed to the gas to be measured; and a reference electrode arranged on the other main plane of said oxygen ion conduction member, which is exposed to a reference gas; wherein said measurement electrode serves as said first combustion catalyst in said first oxygen measurement means and said second combustion catalyst in said second oxygen measurement means.

7. The gas sensor according to claim 6, wherein said oxygen ion conduction member of said first oxygen measurement means and said oxygen ion conduction member of said second oxygen measurement means are integrally formed.

8. The gas sensor according to claim 5, wherein said hydrocarbon prevention filter comprises a zeolite membrane.

9. A method of measuring a hydrocarbon concentration in a gas to be measured by utilizing the gas sensor set forth in claim 5, comprising the steps of: using said first oxygen measurement means to measure a first oxygen concentration in the gas to be measured, from which hydrocarbons are removed by said hydrocarbon prevention filter and further combustible components are removed by said first combustion catalyst; using said second oxygen measurement means to measure a second oxygen concentration in the gas to be measured, from which combustible components are removed by said second combustion catalyst; calculating an oxygen concentration difference between said first oxygen concentration measured by said first oxygen measurement means and said second oxygen concentration measured by said second oxygen measurement means; and calculating a hydrocarbon concentration in a gas to be measured on the basis of the thus calculated oxygen concentration difference.

10. A gas sensor for diagnosing a malfunction of an exhaust gas purifying apparatus in automobiles, comprising: a sensor including a hydrocarbon prevention filter for preventing passage of hydrocarbons therethrough, a combustion catalyst for removing combustible components in a gas to be measured which is passed through said hydrocarbon prevention filter, and oxygen measurement means for measuring an oxygen concentration of the gas to be measured from which said combustible components are removed by said combustion catalyst; and indication means for communicating a malfunction of said exhaust gas purifying apparatus to a driver, when an oxygen concentration difference between said oxygen concentration in the gas measured by said oxygen measurement means and an oxygen concentration in a gas measured by an oxygen sensor for controlling an air/fuel ratio in an engine reaches an oxygen concentration equivalent to a regulation level of hydrocarbons.

11. A method of diagnosing a malfunction of an exhaust gas purifying apparatus by utilizing the gas sensor set forth in claim 10, comprising the steps of: using said oxygen measurement means to measure an oxygen concentration in an exhaust gas passed through said exhaust gas purifying apparatus, from which hydrocarbons are removed by said hydrocarbon prevention filter and further combustible components are removed by said combustion catalyst; calculating an oxygen concentration difference between said oxygen concentration measured by said oxygen measurement means and an oxygen concentration measured by said oxygen sensor for controlling an air/fuel ratio of an engine; and indicating a malfunction of said exhaust gas purifying apparatus to a driver when the thus calculated oxygen concentration difference reaches an oxygen concentration equivalent to a regulation level of hydrocarbons.

* * * * *